United States Patent [19]

Owens et al.

[11] Patent Number: 5,360,893
[45] Date of Patent: Nov. 1, 1994

[54] DNA SEQUENCES ENCODING PROTEINS USED TO ELICIT AND DETECT PROGRAMMED CELL DEATH

[75] Inventors: Gregory P. Owens; J. John Cohen, both of Denver; William E. Hahn, Aurora, all of Colo.

[73] Assignee: University of Colorado Foundation, Inc., Boulder, Colo.

[21] Appl. No.: 915,934

[22] Filed: Jul. 20, 1992

[51] Int. Cl.$^5$ .......................................... C07K 13/00
[52] U.S. Cl. .................................. 530/350; 435/240.1
[58] Field of Search ....................... 435/240.1; 530/350

[56] References Cited

PUBLICATIONS

Evan, G. I., et al., (1992), Cell 69, 119–128.
Itoh, N., et al., (1991), Cell, 66, 233–243.
Lanotte, M., et al., (1991), J. Cell. Physiol., 146, 73–80.
Cohen, J. J., et al., (1984), J. Immun., 132(1), 38–42.

*Primary Examiner*—Charles L. Patterson, Jr.
*Attorney, Agent, or Firm*—Frederick W. Pepper

[57] ABSTRACT

Polypeptides and mutants and variants associated with programmed cell death in mammalian cells and DNA sequences, and fragments and derivatives thereof, encoding the polypeptides are disclosed. Also disclosed are methods for detecting programmed cell death in mammalian cells, a method of activating programmed cell death in unwanted mammalian cells, and methods for preventing unwanted cell death occurring in degenerative disorders of mammals.

2 Claims, 8 Drawing Sheets

II. LIBRARY CONSTRUCTION 1) prime 1st strand cDNA synthesis with Xba I primer adaptor 2) second strand cDNA synthesis – Gruber Hoffman 3) Linker ligation and vector cloning a. fill in-T4 polymerase
    b. linkers ligation – Eco RI
    c. Eco RI and XbaI digestion

**PROGRAMMED LIBRARY
or
CONTROL LIBRARY**

IV. HYBRIDIZE—with in vitro transcribed cRNA

Seperate unhybridized ss DNA

V. Enriched ss DNA

1. PCR amplify and reclone

TRANSFORM COMPETENT CELLS

RP-8   FIGURE 5.A

```
                                                                                    42
     CCG CTC GCC TTC CTG CTG CAA GTG TAC GCA CCG CTT CCG GGT
1    PRO LEU ALA PHE LEU LEU GLN VAL TYR ALA PRO LEU PRO GLY
                                                                                    84
     CGG GAC GAC GCC TTC CAC CGT AGC CTC TTT CTC TTC TGC TGT
15   ARG ASP ASP ALA PHE HIS ARG SER LEU PHE LEU PHE CYS CYS
                                                                                   126
     CGA GAG CCG CTG TGT TGC GCC GGC CTG CGA GTT TTT CGT AAT
29   ARG GLU PRO LEU CYS CYS ALA GLY LEU ARG VAL PHE ARG ASN
                                                                                   168
     CAG CTA CCA AGG AAA AAT GCA TTT TAC TCA TAT GAG CCC CCT
43   GLN LEU PRO ARG LYS ASN ALA PHE TYR SER TYR GLU PRO PRO
                                                                                   210
     TCT GAA ACG GGA GCT TCG GAT ACA GAA TGT GTG TGC CTC CAA
57   SER GLU THR GLY ALA SER ASP THR GLU CYS VAL CYS LEU GLN
                                                                                   252
     CTT AAG TCT GGA GCT CAT CTC TGC AGG GTT TGT GGT TGC TTG
71   LEU LYS SER GLY ALA HIS LEU CYS ARG VAL CYS GLY CYS LEU
                                                                                   294
     GCC CCT ATG ACA TGC TCT AGG TGC AAA CAG GCA CAT TAC TGC
85   ALA PRO MET THR CYS SER ARG CYS LYS GLN ALA HIS TYR CYS
                                                                                   336
     AGC AAG GAA CAT CAG ACA TTA GAC TGG CAG CTC GGC CAC AAG
99   SER LYS GLU HIS GLN THR LEU ASP TRP GLN LEU GLY HIS LYS
                                                                                   378
     CAG GCT TGT ACA CAG TCA GAC CAT TTA GAC CAT ATG GTT CCA
113  GLN ALA CYS THR GLN SER ASP HIS LEU ASP HIS MET VAL PRO
                                                                                   420
     GAC CAT AAC TTG CTG TTT CCA GAA TTT GAA ATT GTA ACA GAA
127  ASP HIS ASN LEU LEU PHE PRO GLU PHE GLU ILE VAL THR GLU
                                                                                   462
     ACA GAA GAC GAG ATT GGG CCT GAG GTG GTG GAA ATG GAG GAT
141  THR GLU ASP GLU ILE GLY PRO GLU VAL VAL GLU MET GLU ASP
                                                                                   504
     TAC TCT GAA GTT ATA GGA AGC ATG GAG GGA GTA CCT GAG GAA
155  TYR SER GLU VAL ILE GLY SER MET GLU GLY VAL PRO GLU GLU
                                                                                   546
     GAA CTA GAT TCC ATG GCA AAG CAT GAA TCC AAG GAA GAT CAC
169  GLU LEU ASP SER MET ALA LYS HIS GLU SER LYS GLU ASP HIS
                                                                                   588
     ATA TTC CAA AAG TTT AAA TCC AAA ATA GCC CTT GAA CCA GAG
183  ILE PHE GLN LYS PHE LYS SER LYS ILE ALA LEU GLU PRO GLU
                                                                                   630
     CAG ATT CTC AGG TAT GGA AGA GGT ATT AAA CCC ATC TGG ATT
197  GLN ILE LEU ARG TYR GLY ARG GLY ILE LYS PRO ILE TRP ILE
                                                                                   672
     TCT GGT GAA AAT ATT CCT CAA GAA AAA GAT ATT CCA GAT TGC
211  SER GLY GLU ASN ILE PRO GLN GLU LYS ASP ILE PRO ASP CYS
                                                                                   714
     TCA TGT GGT GTT AAG AGA ATA TTT GAA TTC CAG GTC ATG CCT
225  SER GYS GLY VAL LYS ARG ILE PHE GLU PHE GLN VAL MET PRO
                                                                                   756
     CAG CTG TTG AAC CAC CTA AAG GCA GAC AGA CTG GGT ACA AGT
239  GLN LEU LEU ASN HIS LEU LYS ALA ASP ARG LEU GLY THR SER
```

RP-8 (CONT.)    FIGURE 5.B

```
                                                                    798
        GTG  GAC  TGG  GGC  ATC  TTG  GCT  GTC  TTC  ACC  TGT  GCT  GAG  AGC
253     VAL  ASP  TRP  GLY  ILE  LEU  ALA  VAL  PHE  THR  CYS  ALA  GLU  SER
                                                                    840
        TGC  AGC  CTG  GGC  ATC  GGG  TTC  ACA  GAA  GAA  TTT  GTG  TGG  AAA
267     CYS  SER  LEU  GLY  ILE  GLY  PHE  THR  GLU  GLU  PHE  VAL  TRP  LYS

CAG  GAT  GTG  ACA  GAG  ACA  CCA  TGA  AAGGTGTTAAATTCTTAAAAATAAA
281     GLN  ASP  VAL  THR  GLU  THR  PRO  ---

TGTTCCTTATGCCTCACTACCTC(A)$_{60}$
```

RP-2  FIGURE 6

```
                                                                          42
      CCC CAG CTG GCA CAT GGC TGC TAC CCA TGC CCT CCA CAC AGG
 1    PRO GLN LEU ALA HIS GLY CYS TYR PRO CYS PRO PRO HIS ARG
                                                                          84
      CGC AAC CTG GTA GAG GAG GTG AAC GGC ACC TAC ATG AAG AAG
 15   ARG ASN LEU VAL GLU GLU VAL ASN GLY THR TYR MET LYS LYS
                                                                         126
      TGC CTC TAT CAC AAG ATT CAA CAC CCC CTG TGC CCA GTC TTC
 29   CYS LEU TYR HIS LYS ILE GLN HIS PRO LEU CYS PRO VAL PHE
                                                                         168
      AAC CTT GGC TAT GTG GTG CGA GAG TCA GGC CAG GAC TTC CGC
 43   ASN LEU GLY TYR VAL VAL ARG GLU SER GLY GLN ASP PHE ARG
                                                                         210
      AGC CTT GCT GAG AAG GGT GGG GTG GTT GGT ATC ACC ATT GAC
 57   SER LEU ALA GLU LYS GLY GLY VAL VAL GLY ILE THR ILE ASP
                                                                         252
      TGG AAG TGT GAT CTG GAC TGG CAC GTT CGG CAC TGC AAA CCC
 71   TRP LYS CYS ASP LEU ASP TRP HIS VAL ARG HIS CYS LYS PRO
                                                                         294
      ATC TAC CAG TTC CAC GGA CTG TAT GGG GAG AAG AAC CTG TCT
 85   ILE TYR GLN PHE HIS GLY LEU TYR GLY GLU LYS ASN LEU SER
                                                                         336
      CCA GGC TTC AAC TTC AGA TTT GCC AGG CAT TTC GTG CAG AAT
 99   PRO GLY PHE ASN PHE ARG PHE ALA ARG HIS PHE VAL GLN ASN
                                                                         378
      GGG ACA AAC CGT CGC CAC CTC TTC AAG GTG TTT GGG ATT CAC
113   GLY THR ASN ARG ARG HIS LEU PHE LYS VAL PHE GLY ILE HIS
                                                                         420
      TTT GAT ATC CTT GTG GAT GGC AAG GCT GGG AAG TTT GAC ATC
127   PHE ASP ILE LEU VAL ASP GLY LYS ALA GLY LYS PHE ASP ILE
                                                                         462
      ATC CCT ACT ATG ACT ACT ATC GGT TCT GGG ATT GGC ATC TTT
141   ILE PRO THR MET THR THR ILE GLY SER GLY ILE [GLY ILE  PHE
                                                                         504
      GGA GTG GCC ACA GTG CTT TGT GAT CTC TTA TTG CTC CAC ATC
155   GLY VAL ALA THR VAL LEU CYS ASP LEU LEU LEU LEU HIS ILE
                                                                         546
      CTG CCT AAG AGG CAC TAC TAC AAG CAG AAG AAG TTC AAA TAT
169   LEU PRO] LYS ARG HIS TYR TYR LYS GLN LYS LYS PHE LYS TYR
                                                                         588
      GCC GAG GAC ATG GGG CCG GGA GAG GGT GAA CAT GAC CCC GTG
183   ALA GLU ASP MET GLY PRO GLY GLU GLY GLU HIS ASP PRO VAL
                                                                         630
      GCC ACC AGC TCC ACT CTG GGC CTG CAG GAG AAC ATG AGG ACC
197   ALA THR SER SER THR LEU GLY LEU GLN GLU ASN MET ARG THR

TCC TGA CCTTAGTCTTGAGATCCGGACTTGACGCAGTGTGTGGCTTCCGGCAAGGGCTG
211   SER ---

ATGGCTTTGAGCCAGGGCAGAGGGCATTCCCAGAGGCTTTCCCTGCAAGGCAGACACCAG
      TGGCCCTCTGGTTCAGCATGAAGACAGGCAAGACTTTGGATTTCATAGCTCTGGTTTCAG
      TTCCACATGTCCCTTCCTGAGGGATGCCTCCTCCAGTTTTCTCCAATTTGGGTTCATATGG
      CTGGGCCC
```

RP-2

| A+ Hrs | 0 | 1 | 2 | 3 | 4 | 6 | 8 |
|---|---|---|---|---|---|---|---|
| %Frag | 8 | 7 | 10 | 41 | 63 | 76 | 77 |

Actin

D+C A+  0 1 2 3 4 6 8

18s rRNA

D+C A+  0 1 2 3 4 6 8

RP-8

D+C A+  0 1 2 3 4 6 8

DNA SEQUENCES ENCODING PROTEINS USED TO ELICIT AND DETECT PROGRAMMED CELL DEATH

The invention described herein was made in the course of work under a grant or award from The Department of Health, Education and Welfare and the Government has certain rights therein.

FIELD OF THE INVENTION

The present invention relates to the diagnostic and therapeutic uses of the first cloned sequences of genes associated with programmed cell death (PCD) in mammalian cells. More specifically, the invention relates to the programmed cell death genes of RP-8 and RP-2.

BACKGROUND OF THE INVENTION

"Programmed" as opposed to "accidental" death of cells is a normal and essential biological feature in the differentiation and maintenance of cellular populations in multicellular organisms. The normal turnover of epithelia such as skin or the gut lining involves the programmed death of terminally differentiated cells. Similarly, many cells of the hematopoietic system have short life expectancies, and their death is also programmed. In the developing nervous system, large numbers of neurons undergo programmed cell death (Oppenheim, Trends Neurosci. 8:487–493 (1985)).

Programmed death can often be distinguished morphologically from accidental death (Wyllie, Int. Rev. Cytol. 17:755–785 (1987); Wyllie, et al., Int. Rev. Cytol. 68:251–300 (1980)). In accidental death, the major target organelle seems to be the mitochondrion, which swells until it is dysfunctional, leading to death and lysis of the cell (necrosis). In contrast, programmed death is usually characterized by an early collapse of the nucleus, with extreme condensation of chromatin and loss of the nucleolus. The cell shrinks, in contrast to swelling in necrosis, and is phagocytosed before it lyses. This phenomenon, first referred to as shrinkage necrosis, is now called apoptosis (Kerr, et al., Br. J. Cancer 26:239–257 (1972)). The nuclear collapse in apoptosis is probably due, in most cell types, to fragmentation of the chromatin into units of single or multiple nucleosomes observable by electrophoresis in agarose gels (Cohen and Duke, J. Immunol. 132:38–42 (1984); Wyllie, Nature 284:555–556 (1980)). This is one of the ways in which apoptosis can be distinguished from necrosis. Chromatin fragmentation may be the result of activation of an endogenous $Ca^{2+}$ and $Mg^{2+}$-dependent endonuclease (Compton and Cidlowski, J. Biol. Chem. 262:8288–8292 (1987); Hewish, Biophys. Res. Commun. 52:475–481 (1973)).

An example of programmed cell death is demonstrated in rodent thymocytes. The death program can be initiated in these cells by a number of inductive stimuli, including exposure to glucocorticoids (Cohen and Duke, J. Immunol. 132:38–42 (1984); Wyllie, Nature 284:555–556 (1980)) and irradiation (Sellins and Cohen, J. Immunol. 139:3199–3206 (1987)). In these instances the death program (apoptosis) can be prevented by the presence of inhibitors of RNA or protein synthesis (Cohen and Duke, J. Immunol. 132:38–42 (1984), Sellins and Cohen, J. Immunol. 139:3199–3206 (1987)). This suggests that genes, normally silent or negatively regulated, are activated by inductive stimuli leading to the production of proteins that mediate or act directly in the death process.

SUMMARY OF THE INVENTION

The present invention provides purified polypeptide products and their mutants and variants associated with programmed cell death in mammalian cells. The particular polypeptides are portions of two previously unknown genes, RP-8 and RP-2. The invention also concerns DNA sequences, and fragments and derivatives thereof, encoding these polypeptide products, antibodies to the polypeptides, and proteins of these previously unknown genes, and host cells involved in the expression of the polypeptide products.

Another aspect of the invention includes a method for detecting programmed cell death in various mammalian cells. This involves generating antibodies that react with the polypeptide and protein products of programmed cell death genes, such as RP-8 and RP-2. Another method for detecting programmed cell death is the use of probes that bind to the RNA of genes associated with programmed cell death of various mammalian cells.

A further aspect of the invention involves a method of activating programmed cell death in unwanted mammalian cells. Included among these cells are cancer cells and immune cells linked to autoimmune diseases. Cell death activation is accomplished by selectively activating a gene, such as RP-8 or RP-2, that expresses a protein which elicits programmed cell death in the unwanted cell.

An additional aspect of the invention involves a method for preventing unwanted cell death occurring in a degenerative disorder of a mammal. Degenerative disorders known to involve cell death are Alzheimer's disease, Parkinson's disease, and Huntington's disease. Compounds used in preventing unwanted cell death can be antibodies to a protein associated with programmed cell death in such disorders or drugs designed to inhibit the activity of such a protein. In addition, the use of oligonucleotides complementary to an mRNA associated with programmed cell death can prevent unwanted cell death in such disorders.

BRIEF DESCRIPTION OF THE DRAWINGS

FIG. 5 (SEQ ID NO: 1) represents the nucleotide sequence and amino acid sequence of the sense strand of clone RP-8; and FIG. 6 (SEQ ID NO: 3) represents the nucleotide sequence and amino acid sequence of the sense strand of clone RP-2.

DETAILED DESCRIPTION OF THE INVENTION

Figure 1A:
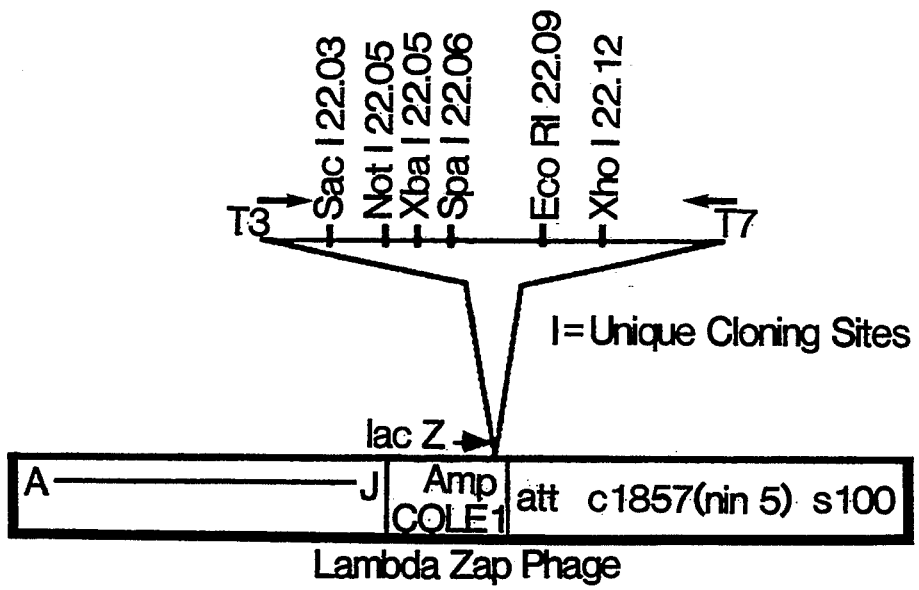
FIG. 1 shows a schematic outline of a cloning procedure leading to construction of a subtracted library enriched for sequences expressed in death-induced thymocytes.
Figure 1A:
Figure 1A:
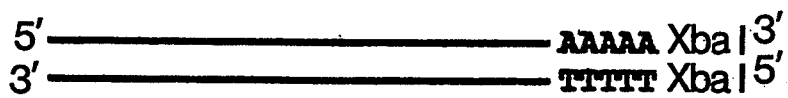
Figure 1A:
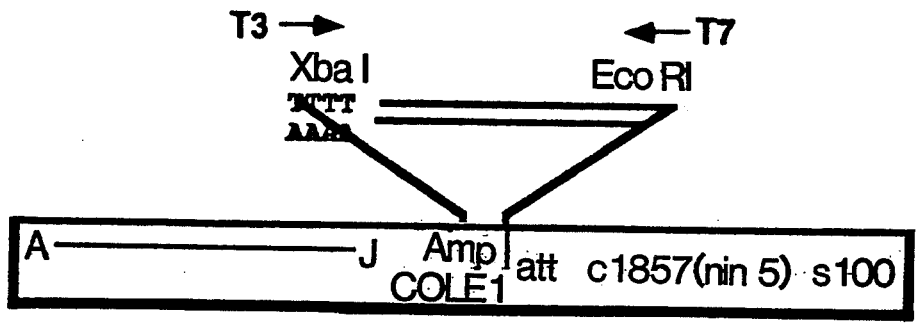
Figure 1B:
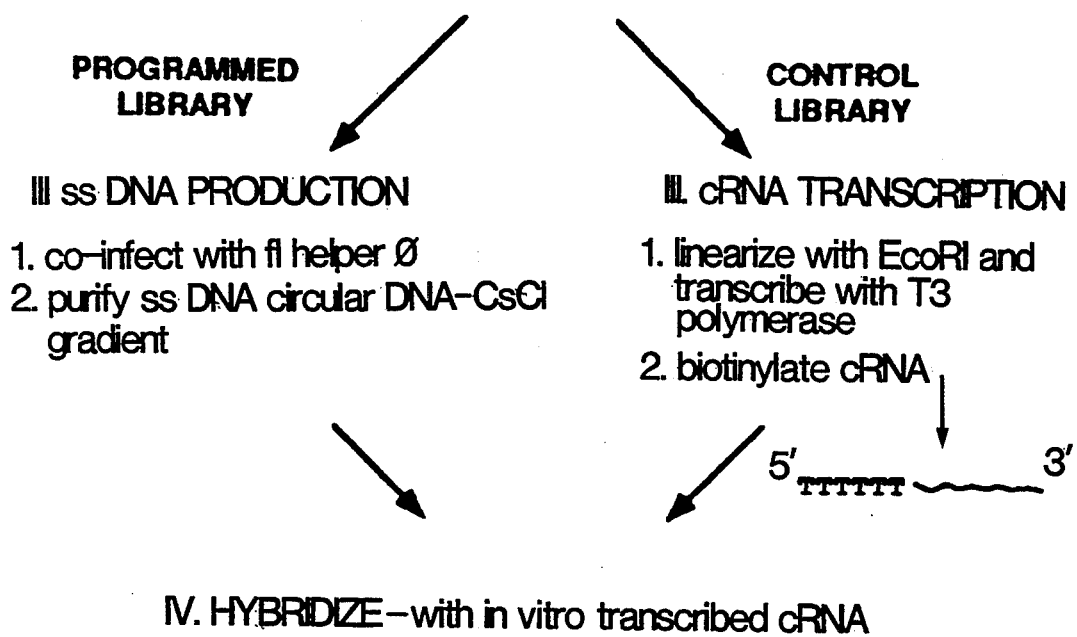
Figure 1B:
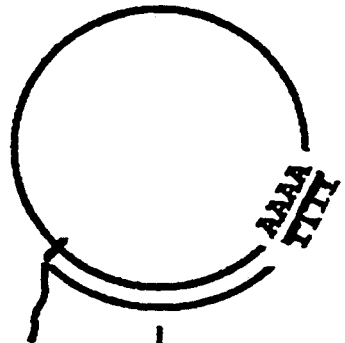
Figure 1B:

A cDNA library is constructed that is enriched for sequences expressed in thymocytes induced to die. To construct this library, a directional cloning strategy is devised by combining certain recent procedural advances that have been used to produce subtracted (enriched) cDNA libraries (Duguid et al., Proc. Natl. Acad. Sci. U.S.A. 85:5738–5742 (1988); Palazzolo and Meyerowitz, Gene 32:197–206 (1987); Sive and St. John, Nucleic Acids Res. 16:10937 (1988)). Various types of procedures for subtractive hybridization have resulted in the isolation of clones corresponding to the T-cell receptor (Hedrick et al., Nature 308:149–153 (1984)); a muscle-specific regulatory protein, myogenin (Wright et al., Cell 56:607–617 (1989)); genes expressed in growth-arrested cells (Schneider et al., Cell 54:787–793 (1988)); mRNAs in scrapie-infected brains (Duguid et al., Proc. Natl. Acad. Sci. U.S.A. 85:5738–5742 (1988)); and mRNAs in the cortex of the brain (Travis and Sutcliffe, Proc. Natl. Acad. Sci. U.S.A. 85:1696–1700 (1988)). From a library enriched for cDNA representing mRNAs specifically present in death-induced cells, cloned cDNAs complementary to mRNAs are isolated that appear soon after cells are exposed to a stimulus that triggers programmed cell death. These mRNAs are considered to be potential "death gene" products since their presence is death associated, and not simply single-stimulus associated.

RP-2 and RP-8 are death-associated mRNAs that appear upon induction by stimuli that are known to trigger expression of a death program in thymocytes. RP-2 and RP-8 mRNAs are detected at different times following induction of death by irradiation, and they both accumulate in the cytoplasm when the mRNA specifying the abundant protein actin is declining.

RP-2 and RP-8 mRNAs are not unique to thymocytes and they appear upon induction of death in other types of cells, such as epithelial cells and neurons. Expression is shown to be associated with death induced by different stimuli in other types of cells which show that RP-2 and RP-8 are involved in programmed cell death.

Both RP-2 and RP-8 mRNAs specify proteins that are essential in programmed cell death, as is apparently the case of the products from ced-3 and ced-4 genes in the nematode *Caenorhabditis elegans* (Yuan and Horwitz, Der. Biol. 138:33–41 (1990)). In this regard, the zinc finger protein encoded by RP-8, which is expressed soon after induction before morphological changes are apparent, functions as an essential regulatory component. Therefore, the use of complementary oligonucleotides perturb or block programmed cell death. Such oligonucleotides are readily taken up by mammalian cells in culture, leading to hybridization-based blockage of translation or the degradation of specific mRNAs.

The RP-2 and RP-8 mRNAs are death associated because they are isolated from a library constructed with mRNA from dexamethasone and cycloheximide-treated thymocytes and they are also shown to be expressed at increased levels in irradiated thymocytes. Since RP-2 and RP-8 mRNAs are consistently expressed in a variety of cell types induced to die by a number of different stimuli, they are involved in the process of programmed cell death.

Construction Of A Library Enriched For Sequences Expressed In Death-Induced Thymocytes In order to obtain an enriched or subtracted library, two source cDNA libraries are first constructed to provide a convenient supply of copy RNA and cloned cDNA molecules. The "programmed" library represents mRNA from thymocytes induced (or programmed) to die by exposure to dexamethasone in the presence of cycloheximide. The "control" library represents mRNA from untreated thymocytes. The cDNA libraries are constructed such that the cDNA inserts in each of the two libraries are oriented in the cloning vector, Lambda Zap, in the same direction (directional cloning). Dying cells present a unique problem in preparing poly(A)+mRNA used in the construction of these libraries. Virtually nothing is known about the number of genes that encode the death program or their temporal expression following exposure to the death stimulus. Since the basic strategy for cloning putative death genes is based upon their unique or increased expression in dying cells, the time following induction when RNA is harvested for library construction could significantly influence screening results. This uncertainty is compounded further by the fact that in apoptotic cells much of the RNA is degraded (Cidlowski, Endocrinology 111:184–190 (1982)). To have as many cells as possible in the population committed to the death program, while avoiding the isolation of RNA from cells where accelerated degradation might be occurring, cycloheximide is added to the culture medium at the time of induction. Cycloheximide blocks protein synthesis and prevents expression of death processes, while allowing expression at the nucleic acid level (Sellins and Cohen, J. Immunol. 139:3199–3206 (1987)). Thus, mRNA accumulates under these conditions in death-induced thymocytes. To ensure that the death program is induced at the time cells are harvested for making RNA, a small aliquot of cells is removed from the induced culture and washed free of cycloheximide and inducer. These cells are then continued in a subculture; all cells die within 8 to 12 h. A second point regarding mRNA preparation pertains to the control, or noninduced, culture of thymocytes. Of thymocytes removed from the thymus, about 5 to 10% are in various phases of the death process as they are placed in culture. Thus, in preparing template mRNA for the cDNA used to produce the control library, as many of the dying cells are first removed as possible by centrifugation through a Percoll gradient (Wyllie and Morris, Am. J. Pathol. 109:78–87 (1982)).

FIG. 1 provides an overview of the strategy that is applied to produce the enriched or subtracted library by using these two cDNA libraries. Directional cloning can be achieved by use of any two of the unique restriction endonuclease sites present in the promoter-flanked multiple cloning site of the vector. In this case, a primer-adaptor oligonucleotide is used containing the base sequence recognized by XbaI endonuclease to primer first-strand cDNA synthesis (FIG. 1).

Double-stranded cDNA is obtained by the RNase-H digestion and DNA polymerase fill-in method of Gubler and Hoffman (Gene 25:263–269 (1983)). The resultant double-stranded cDNA is blunt ended by using T4 polymerase and oligonucleotide linkers containing the EcoRI restriction sequence are then ligated to the cDNA. To prepare the cDNA for insertion into Lambda Zap, digestions are performed by using EcoRI and XbaI endonucleases. This cDNA inserts into similarly cut vector so that when the recombinant phage is used in helper phage-assisted production of closed circular ssDNA from the programmed library, the resultant ssDNA is sense strand (i.e., complementary to cDNA).

Since insertion is directionally controlled rather than random, the cloned sequences in the control library can be transcribed in vitro as either sense or antisense RNA molecules by using the T3 and T7 promoter sites present at opposite sides of the cloning region. As shown in FIG. 1, use of T3 polymerase yields antisense RNA, and T7 polymerase, which transcribes the opposite strand, produces sense RNA (i.e., equivalent to mRNA).

The control and programmed libraries provide RNA and ssDNA to use for subtractive hybridization of cDNAs representing mRNAs shared between control and induced cells (the bulk of the different cloned sequences). Hybridization driven with biotinylated antisense copy RNA from the control library removes about 97% of the sense strand insert-containing ssDNA present in the programmed library. See Table 1 below.

TABLE 1

| | Subtractive hybridization with copy RNA | | |
|---|---|---|---|
| ssDNA | Driver RNA | $c_0t$ | % Hybridization |
| Phagemid-cDNA | Copy RNA (T3) | 1.200 | 97 |
| SK(−) | Copy RNA (T3) | 1.700 | 14 |
| SK(−) | Copy RNA (T7) | 1.700 | 12 |
| SK(−) | Yeast tRNA | 1.700 | 0 |

As shown in Table 1, ssDNA (see examples below) from the programmed library was iodinated, and the recombinant (phagemid+inserted cDNA) molecules were isolated by electrophoresis in agarose gels. SK(−), $^3$H-labeled vector ssDNA. Copy RNA was obtained by in vitro transcription of cDNA in the control library. Sense and antisense molecules were produced by using T7 and T3 polymerase, respectively.

Fractionations, for determining the extent of hybridization, are done by use of the streptavidin-phenol-chloroform extraction method (Sive and St. John, Nucleic Acids Res. 16:10937 (1988)). Control experiments are performed to determine the specificity of the hybridization of thymocyte sequences. Because the copy RNA (T3 products) used as driver contains ∼50 nucleotides of SK(−) vector sequence, because of the position of the T3 promoter initiation site, it is important to show that the subtractive hybridization of ssDNA is due to the presence of cloned cDNA rather than vector sequences. As shown in Table 1, under the conditions used, these vector sequences contribute only slightly to hybridization.

Figure 2:
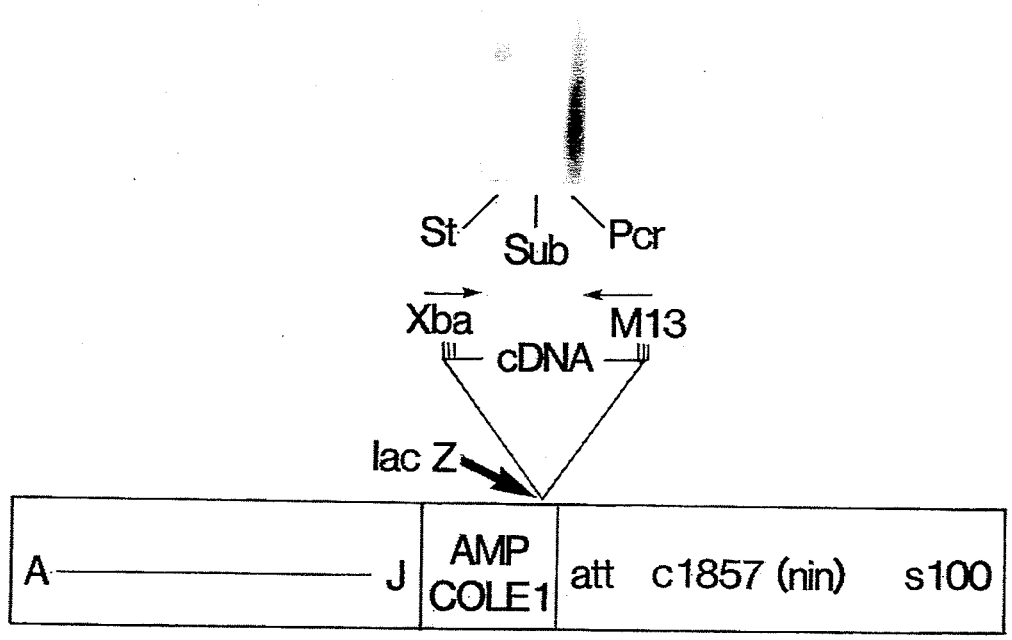
FIG. 2 represents a DNA blot showing effectiveness of subtractive hybridization and Taq polymerase (PCR) amplification of subtracted ssDNA.

Since Table 1 establishes that shared cDNA sequences are effectively removed, total ssDNA (see examples) is used in subtractive hybridization to obtain cDNA for enriched library construction. Nonhybridized cDNA is considered to be greatly enriched for sequences present in the mRNA from programmed (dying) cells but absent or rare in control cells. The ssDNA recovered after hybridization that is used in the PCR mixture consists of SK(−) vector DNA lacking inserts, unhybridized SK(−) vector containing cDNA inserts, and VCS-M13 helper phage DNA. However, only the enriched cDNA is carried forward from this mixture into the construction of the subtracted library because the cDNA is selectively primed in conducting PCR. This amplification is performed by using the XbaI oligo (dT) primer-adaptor in conjunction with the universal M13 primer that flanks the multiple cloning site. The effectiveness of both the amplification and subtractive hybridization is shown in FIG. 2. In the far left lane of FIG. 2, hybridization of ssDNA with labeled cDNA from control cell mRNA is shown. The center lane of FIG. 2 (Sub) shows lack of discernible cDNA hybridization to subtracted ssDNA. One microgram of DNA is applied in each of these two lanes. The lane at the far right of FIG. 2 shows hybridization of cDNA to the denatured double-stranded DNA produced by PCR upon selective priming of the ssDNA remaining after subtractive hybridization. Cloned cDNA that is amplified is contained in the region of the vector as shown in FIG. 1. As the migration of double-stranded DNA differs markedly from that of ssDNA, molecular distribution in the gel is not directly comparable. Also, the PCR product contains concatemers. The vector and helper phage DNAs, while present in the mixture, are not amplified by this procedure. The PCR-amplified cDNA sequences, which retain their XbaI and EcoRI sites, are appropriately digested and inserted into pBluescript vector KSM13(+) to produce a library enriched for sequences that are enhanced or specifically expressed in death-induced cells (see examples).

Screening and Selection of Clones From the Enriched, Subtracted Library

The enriched library is screened by colony blot hybridization with cDNA representing mRNA from control and induced (dexamethasone- and cycloheximide-treated) cells. Before use, the cDNA transcribed from mRNA from induced cells is subtracted by hybridization with mRNA from control thymocytes. Using the subtracted probe, 24 hybridizing colonies are identified from approximately 1,000 recombinants and are evaluated for duplication by cross hybridization in Southern blots.

Evaluation of Selected Clones

The evaluation of cloned cDNAs for potential correspondence to genes activated in programmed cell death is complicated. First, the thymocytes in the control and induced cultures are not synchronous or homogeneous. In short-term control cultures, about 3 to 8% of the cells are expected to be dying at the time we extracted RNA (Cohen and Duke, J. Immunol. 132:38–42 (1984)), and therefore, are presumed to have expressed gene products that might be involved in the death process. In other words, a truly null control population of thymocytes is not available, even after Percoll fractionation, and hence search and evaluation is based on mRNAs showing either a restricted observable presence or increased abundance in induced cells. Second, following exposure to dexamethasone, all cells in the culture do not respond synchronously (Thomas and Bell, Mol. Cell. Endocrinol. 22:71–84 (1981)). Thus, in order to have most of the cells entered into the death process, it is necessary to maintain them for 6 to 8 h following induction. This period of time presents a problem in that much of the mRNA in dying cells is degraded. As shown below, within about 4 to 6 h following induction, actin mRNA ss no longer detectable by the standard Northern blot procedure. Therefore, to stabilize mRNAs, including those that may be the products of genes that are activated by the inductive stimulus, cycloheximide is used to block protein synthesis, as previously explained. However, exposure to cycloheximide alone can result in cell death. It is found that when thymocytes are treated with cycloheximide for 4 to 6 h and then the block is released by washing, increased DNA fragmentation and cell lysis are observed over the next several hours (Sellins and Cohen, J. Immunol. 139:3199–3206 (1987)). This suggests that, in immature thymus cells, cycloheximide directly or indirectly induces cell death processes or that the production of cell death messages may be constitutive at a low level; cycloheximide allows these messages to accumulate, and after the protein synthesis block is removed, they are expressed. Despite these complications, clones of potential interest can be evaluated by using mRNA from irradiated or dexamethasone-treated cells that are maintained in the presence or absence of cycloheximide.

Northern Blot Analysis

Figure 3:
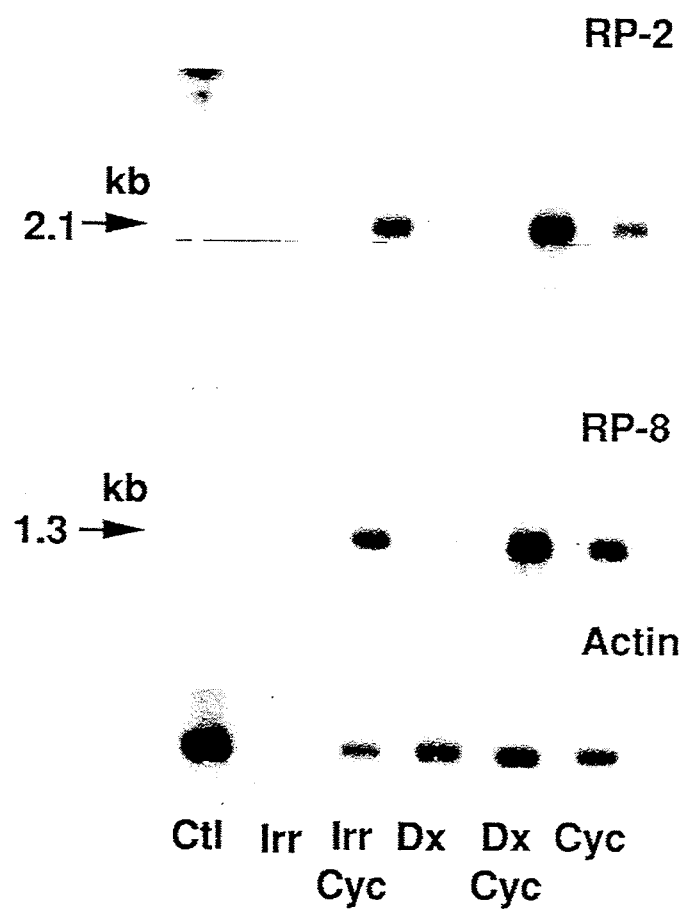
FIG. 3 shows Northern blot analysis of candidate clones, RP-2 and RP-8.

Northern blots are prepared and probed with candidate cDNAs. An example of this further evaluation is shown for cDNAs RP-2 and RP-8 (FIG. 3). As shown in FIG. 3, poly(A) cytoplasmic RNA (2 µg) from control (Ctl), irradiated (Irr), irradiated+cycloheximide-exposed (Irr Cyc), dexamethasone-treated (Dx), dexamethasone-cycloheximide-treated (Dx/Cyc), and cycloheximide-exposed (Cyc) cells are subjected to electrophoresis in a 1% agarose gel. The RNA is then transferred to Hybond nitrocellulose and hybridized with RP-2 cDNA. Blots are then erased, hybridized with RP-8 CDNA, and finally erased and reprobed with actin cDNA. The sizes of hybridizing RNA species are determined by comparison with the electrophoretic migration of RNA standards. RP-2 is found to be complementary to a 2.1-kb mRNA and RP-8 is shown to be complementary to a 1.3-kb mRNA present in increased abundance in both irradiated and dexamethasone-induced cells that are maintained in the presence of cycloheximide. Both mRNAs are also elevated in cells treated with cycloheximide alone. In this Northern blot, modest increases relative to control cell RNA are observed for RP-2 and RP-8 mRNAs from cells treated only with dexamethasone for 4 h, but not in cells 4 h after exposure to radiation. The effect of cycloheximide on mRNA abundance can be clearly seen by comparing the Northern blot signals between stimulus-plus-cycloheximide-treated cells and cells receiving only irradiation or dexamethasone. The lower levels of RP-2 and RP-8 mRNAs in cells treated only with dexamethasone or irradiation is probably a reflection of the mRNA abundance and integrity in general in these populations of cells at the time RNA is harvested. This is particularly striking in irradiated cells, where even normally abundant actin mRNA is only weakly detected.

Temporal Appearance of Candidate mRNAs

After identifying RP-2 and RP-8 as mRNAs that appear in death-induced thymocytes, in the presence of cycloheximide, a determination is made whether these mRNAs can be detected at various times after induction in cells that are not maintained in the presence of cycloheximide. It is important to establish that the induction of these mRNAs is not simply an artifact of cycloheximide treatment. Detection of these mRNAs in the cytoplasmic fraction, even without the stabilizing influence of cycloheximide, is possible provided RNA is harvested soon after expression is induced, before nuclear disorganization and nucleic acid degradation is advanced in a large number of cells in the culture. Because the time frame of early events in programmed cell death is only roughly known, cytoplasmic RNA is prepared from cultures at 1 h intervals following irradiation. Irradiation is elected as the inductive stimulus because it evokes a more synchronous response, and it is a stimulus different from that given to cells (dexamethasone and cycloheximide) that are represented in the programmed library.

Figure 4:
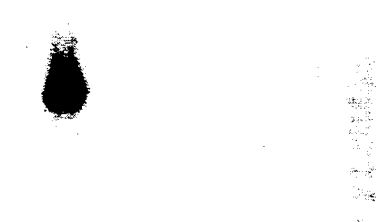
FIG. 4 shows temporal appearance of RP-2 and RP-8 mRNAs in thymocytes following low-dose gamma irradiation.
Figure 4:
Figure 4:

The temporal appearance of RP-2 and RP-8 mRNAs in thymocytes following low-dose gamma irradiation is shown in FIG. 4. Northern blot analysis was performed on total cytoplasmic RNA isolated from thymocytes at 0, 1, 2, 3, 4, 6, and 8 h after irradiation. In each lane, 20 µg of RNA is applied. The blot is hybridized with the following cDNAs: RP-2, RP-8, actin, and an antisense 18S rRNA oligonucleotide. RP-2 mRNA appears in thymocytes 2h following irradiation but is no longer detectable after 6 h. RP-8 is detectable after 1 h following exposure and likewise is no longer detected in cells 6 h following exposure. As these cells are not stabilized by the addition of cycloheximide, actin mRNA also declines following irradiation and is only faintly detectable, if at all, after 6 h. In comparison, rRNA is relatively stable throughout this period when the death process is ongoing. For reference, poly(A) cytoplasmic RNA (A+, 2 µg) in the first lane of each panel from dexamethasone-cycloheximide-treated cells (D+C) is shown. % Frag represents percentages of DNA fragmentation (are determined as previously described (Sellins and Cohen, J. Immunol. 139:3199–3206 (1985)) in the culture at various times following irradiation.

As shown in FIG. 4, the 2.1 kb RP-2 mRNA species is detectable in whole cytoplasmic RNA (mass mostly rRNA) at about 2 h following irradiation, and it is most abundant at 3 h. This is particularly striking, as at 3 h actin mRNA has already markedly declined. Thus, despite apparent highly degradative conditions RP-2 mRNA accumulates. Using the total cytoplasmic RNA rather than the poly(A) fraction, a variant species of ~3.4 kb is also detected in the 3-h sample. This can be another form of this mRNA, or it might be a primary or partially processed transcript that is released as a consequence of a developing nuclear lesions. At 4 h, RP-2 mRNA is mostly degraded and thus appears as a smear of smaller molecules rather than a 2-kb band. By 6 h postirradiation, RP-2 sequences are only faintly detectable, if at all. The presence of hybridizing higher-molecular-weight molecules, noticeable at 4 h postirradiation, is likely due to nuclear leakage to the cytoplasmic fraction of cleaved, genomic DNA and unprocessed primary transcripts or fragments thereof. The appearance of RP-2 mRNA seems to be late in the program, as it precedes or coincides with extensive breakdown of chromatin characteristic of dying cells. As given in FIG. 4, 63% of the chromatin in the induced culture is fragmented by 4 h postirradiation.

The appearance of RP-8 mRNA is detected in advance of RP-2 when the same Northern blot is probed. This 1.3-kb species is elevated within 1 h following irradiation. RP-8 also differs from RP-2 mRNA in that its abundance is greatest at 1 to 2 h following induction, and it shows a decline at 3 h after induction, when RP-2 mRNA is highest. RP-8 mRNA remains detectable at 4 h, although by 4 h, just as in RP-2 sequences, hybridization reveals a smear rather than a band of molecules.

The Northern blot shown in FIG. 4 is also reprobed with actin cDNA as an internal control for mRNA integrity. Noticeable reduction in its abundance is detected at 3 h, and like RP-2 and RP-8 mRNAs, actin mRNA is mostly eliminated 6 h following induction of cell death. An oligonucleotide complementary to 18S rRNA is used to probe the Northern Blots, and as shown this relatively stable, protein-complexed RNA remained largely intact throughout the sampling period even though mRNAs are degraded.

Sequence Analysis of Death-Associated mRNAs

The initial cDNAs isolated for clones RP-8 and RP-2 are rather small being 210 and 650 nucleotides in length respectively. To isolate larger cDNAs and to avoid the direct sequencing of PCR-generated molecules, the programmed lambda libraries are screened, with RP-8 and RP-2 clones as probes, and additional cDNA clones are obtained. For RP-8, the longest insert obtained is 960 nucleotides and for RP-2, the longest insert is about 1,850 nucleotides.

The nucleotide sequence and amino acid sequence of RP-8 is shown in FIG. 5 (SEQ ID NO: 1). There exists from the 5' end of the cDNA an open reading frame of 861 nucleotides followed by a short 3' untranslated region of 49 nucleotides and a poly (A) tail. The open reading frame contains a cysteine-rich region that is characteristic of zinc finger and metallothionein proteins. A putative zinc finger of the C2H2 type (Evans and Hollenberg, Cell 52:1–3 (1988)) begins at residue 81. This single zinc finger (C-X-C-X12-H-X5-H) contains five amino acids between histidine residues instead of the usual three found in most of the reported C2H2 zinc fingers. Proteins known to have this spacing between histidine residues include hunchback (Tautz, et al., Nature 327:383–389 (1987)), teashirt (Fasano, et al., Cell 64:63–79 (1991)), and the Suvar (Chirgwin, et al., Biochemistry 18:5294–5299 (1979); Compton and Cidlowski, J. Biol. Chem. 262:8288–8292 (1987); Reuter, et al., Nature (London) 344:219–223 (1990)) proteins from Drosophila spp. and human PRDIIBFI (Fan and Maniatis, Genes Dev. 4:29–42 (1990)).

A partial sequence of clone RP-2 is presented in FIG. 6 (SEQ ID NO: 3). Only the portion of the 1.8-kb insert that has been sequenced in both strands is shown. The sequence contains an open reading frame beginning immediately at the 5' end of the cDNA and ending 633 nucleotides downstream. Two additional in-frame stop codons are also found 6 and 12 nucleotides from the first terminations signal. The 3' untranslated region of RP-2 is quite long, being about 1,200 nucleotides in length, of which only 218 nucleotides is shown in FIG. 6 (SEQ ID NO: 3). The cDNA clone also contains a poly(A) tail and polyadenylation signal. RP-2 cDNA is expressed in a bacterial expression vector, and the size of the induced fusion protein is consistent with the length of the open reading frame predicted from cDNA sequencing. Structural analysis of the open reading frame classifies RP-2 as an integral membrane protein (Klein, et al., Blochim. Biophys. Acta 815:468–476 (1985)) with a 17 amino-acid hydrophobic membrane-spanning domain and a 41-amino acid cytoplasmic domain. A membrane-associated alpha helix predicted by several methods (Eisenberg, et al., J. Mol. Biol. 179:125–142; Rao and Argos, Biochim. Biophys. Acta 869:197–214 (1986)) runs from glycine 152 to proline 170. Two potential N-glycosylation sites are located upstream from the membrane-spanning domain.

In Situ Hybridization of RP-8

A. Probe Labeling

Synthetic oligonucleotide anti-sense probes for RP-8 (20-22 mers) are used for in situ hybridization experiments. Probes are labeled at the 3'-end with $^{35}$S-dATP (Amersham) with terminal transferase (Strategene). After the labeling reaction, labeled oligonucleotides are separated from unincorporated $^{35}$S-dATP by purification on a Sephadex G-25 "spin column" (Boehringer Mannheim). This method is used to label probes with specific activities between 2–5×10 dpm/ug. For control hybridizations, oligonucleotide sense probes are labeled. The control probes allow assessment of the extent of non-specific binding.

B. Preparation Of Slides, Hybridization, And Washing

Epithelial sections are floated off the slides in 1× SSC. The sections are then placed in 25–50 ul of a hybridization solution consisting of 4× SSC with 50% deionized formamide, 1× Denhardt's solution with 10% dextran sulfate, sonicated salmon sperm DNA (500 ug/ml), 10 mM dithiothreitol, and 250,000 cpm/100 ul of labeled oligonucleotide for 12–16 hours at 32° C. The sections are transferred to petri dishes and washed for 30 minutes in 1× SSC at room temperature, next, in 0.2× SSC at 38° C., and finally in 0.2× SSC at room temperature. Sections are mounted on slides for autoradiography.

Expression of RP-8 In Cells

Using nucleotide sequences contained within the RP-8 protein encoding region as probes in an in situ hybridization procedure, expression is observed of the RP-8 protein in several types of cells discussed below.

The RP-8 sequence is used to probe granular neurons in the cerebellum that undergo cell death in the mutant mouse (weaver). Cell death occurs during early postnatal development in these animals (Symyne and Goldwitz, J. Neurosci. 9:1608–1620 (1989)). The RP-8 sequence is found by in situ hybridization, to be expressed in cells positioned in the external granular layer of the cerebellum.

In the normal adult liver a low level of programmed cell death (as assumed from the presence of apoptotic cells) occurs. RP-8 expression is observed in fewer than one cell in about 5000. The rare expression of RP-8 is consistent with the frequency of the presence of apoptotic cells.

The thymus gland from adult rats that are untreated or treated with glucocorticoid are examined by in situ hybridization. Glucocorticoids raise the level of PCD in the thymic lymphocytes. Expression of RP-8 is observed to be increased about 2-fold in thymus glands from the steroid treated animals. Thus, increased expression (number of cells with RP-8 sequences) is linked with increased programmed cell death in the thymus gland.

Sensory cells of the olfactory region of the nasal passageway are continuously renewed. Some of the new sensory cells fail to migrate and establish functional connections with olfactory nerve fibers and they die. When the olfactory epithelium is probed, expression of RP-8 is observed in cells located in the region where programmed cell death is thought to occur in cells that fail to migrate.

These examples indicate that RP-8 expression is a marker for the process of programmed cell death in several types of cells in addition to thymocytes.

Deposit Of Strains Useful In Practicing The Invention

A deposit of biologically pure cultures of the following strains was made with the American Type Culture Collection, 12301 Parklawn Drive, Rockville, Md., the accession number indicated was assigned after successful viability testing, and the requisite fees were paid.

Access to said culture will be available during pendency of the patent application to one determined by the Commissioner to be entitled thereto under 37 C.F.R. Section 1.14 and 35 U.S.C. Section 122. All restriction on availability of said culture to the public will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture(s) of the same taxonomic description.

The RP-8 cDNA sequence, inserted into the plasmid pBluescript SKM13(−) in the strain E. coli XL-Blue, has been given ATCC No. 69031 and deposit date, Jul. 14, 1992. The RP-2 cDNA sequence, inserted into the plasmid pBluescript SKM13(−) in the strain E. coli XL-Blue, has been given ATCC No. 69032 and deposit date, Jul. 14, 1992.

The RP-2 and RP-8 genes and their gene products, as will be apparent to those of skill in the art, are useful in the treatment and diagnosis of human diseases. In the treatment of a particular disease, such as cancer, they are useful in that the selective activation of the genes leads to the expression of proteins which signal the onset of the programmed cell death for the cancer cells. Another use for the RP-2 and RP-8 genes is their selective elimination of immune cells linked to autoimmune diseases. As in the cancer cells, selective activation of the RP-2 and RP-8 genes results in expression of a protein that eliminates those immune cells active in the autoimmune disease. A therapy which utilizes the body's own genes such as RP-2 and RP-8 to selectively treat cancer can lessen or eliminate the need for chemotherapy. Chemotherapy is not selective and often weakens the patient more than the cancer.

A knowledge of the RP-2 and RP-8 gene products are useful in designing drugs for treatment of neurodegenerative diseases. Drugs designed to inhibit the activity of these gene products can block unwanted cell death as it occurs in neurodegenerative diseases. In the case of an antibody designed drug there is inhibition of the protein activity. With an oligonucleotide designed drug, an oligonucleotide is designed to be complementary to the mRNA of the gene associated with the unwanted cell death. Inhibition of mRNA activity occurs by hybridization-based blockage of translation or the degradation of specific mRNAs.

RP-2 and RP-8 and their gene products are of considerable use in monitoring the extent of cell death associated with specific diseases. Once the severity of the disease is assessed from the amount of RP-2 or RP-8 gene product present, a physician can then determine the course of treatment.

The following examples are presented to illustrate the present invention and to assist one of ordinary skill in making and using the same. The examples are not intended in any way to otherwise limit the scope of the invention.

EXAMPLE 1

Preparation And Culture Of Thymocytes

Single-cell suspensions were prepared and cultured from the thymuses of 4- to 6-week-old male Sprague-Dawley rats by using the procedures and tissue culture medium previously described (Sellins and Cohen, J. Immunol. 139:3199–3206 (1987)). Steroid-induced thymocytes were cultured for the indicated periods in the presence of $10^{-6}$ M dexamethasone (Cohen and Duke, J. Immunol. 132:38–42 (1984)). Where indicated, 50 μg of cycloheximide per ml was also included in the culture medium. Thymocytes exposed to irradiation received 900 R from a $^{60}$Co source (Sellins and Cohen, J. Immunol. 139:3199–3206 (1987)).

EXAMPLE 2

Isolation Of Total Cytoplasmic RNA From Thymocytes

Total cytoplasmic RNA was isolated from thymocytes by using the protocol of either Chirgwin et al. (Biochemistry 18:5294–5299 (1979)) or Chomczynski and Sacchi (Anal. Biochem. 162:156–159 (1987)), following the removal of nuclei by low-speed centrifugation. Polyadenylated RNA was obtained by oligo(dT) chromatography, and total cellular polyadenylated RNA was obtained by using the Fast Track mRNA kit (Invitrogen, San Diego, Calif.). RNA was prepared from control thymocytes immediately after the preparation of single-cell suspensions.

EXAMPLE 3

Construction Of Directionally Cloned cDNA Libraries From Thymocytes

Directionally cloned cDNA libraries were constructed by using polyadenylated cytoplasmic RNA from control thymocytes and thymocytes cultured 8 h in the presence of dexamethasone and cycloheximide. To minimize programmed cell death in the control population animals were adrenalectomized 2 weeks prior to RNA isolation. Also, at the time of harvest, apoptotic cells were removed from the control cell suspensions by Percoll gradient sedimentation (Wyllie and Morris, Am. J. Pathol. 109:78–87 (1982)).

First-strand cDNA was synthesized by using an oligo(dT) primer-adapter (Promega, Madison. Wis.) containing an XbaI restriction site 5' to the oligo(dT) tail. Reaction mixtures (200 μl) contained 5 to 10 μg of polyadenytated RNA in standard reverse transcriptase buffer (50 mM Tris-HCl, pH 8.0, 8 mM MgCl$_2$, 50 mM KCl, 1 mM dithiothreitol, 50 μg of RNase-free bovine serum albumin per ml), 5 mM deoxynucleoside triphosphate (dNTP), 12.5 μg of primer per ml, 1 U of human placental RNase inhibitor per μl, 50 μg of actinomycin D per ml, and 20 to 25 U of reverse transcriptase (Life Sciences Inc.). To monitor synthesis, 20 μCi of [$^{32}$P]dCTP (3,000 Ci/mmol) was included in the reaction mixture. Second-strand cDNA was synthesized by using the procedures described by Gubler and Hoffman (Gene 25:263–269 (1983)).

The cDNA was blunt ended by using T4 polymerase (Bethesda Research Laboratories) and then methylated by using EcoRI methylase (New England BioLabs). EcoRI linkers radioactively labeled and phosphorylated with polynucleotide kinase (Boehringer Mannheim) were ligated to 200 to 500 ng of cDNA with T4 DNA ligase (New England BioLabs) during a 12 h incubation at 15° C. Following the ligation of linkers, reactions were diluted and digested sequentially with EcoRI and XbaI. Digested linkers were separated from cDNA by three ethanol precipitations in the presence of 2.2M ammonium acetate. pH 5.2, followed by one precipitation in 0.3M sodium acetate, pH 5.2. Digestion of linkers was monitored by electrophoresis in 2% agarose gels and autoradiography. A second round of digestions was often required to completely cut the ligated linkers. Final cDNA pellets were resuspended in 10 to 20 μl of sterile 0.1 × TE buffer (1 × TE buffer is 10 mM Tris-HCl, pH 7.4,2 mM EDTA).

Different amounts of double-stranded cDNA were ligated to appropriately digested Lambda Zap I (Stratagene Cloning Systems, La Jolla, Calif.) by using their recommended conditions. Ligated vector DNA was then inserted into phage particles by using the Gigapak Plus-6 packaging system (Stratagene Cloning Systems). Amplified stocks were prepared from infected *Escherichia coli* BB4 (Maniatis, et al., Cold Spring Harbor Laboratory, Cold Spring Harbor, N.Y. (1982)).

A second cDNA library from programmed cells was also prepared as just described except that NotI linkers were used to clone cDNA into Lambda Zap. This library was used to isolate larger cDNA inserts.

EXAMPLE 4

Preparation Of Phage DNA

Synthesis and isolation of phagemid DNA was essentially done by following the Stratagene protocol. The host *E. coli* strain XL1-Blue was grown in 2× YT medium supplemented with tetracycline (12.5 μg ml). At an $A_{600}$ of 0.4 to 0.5 ($3 \times 10^8$) to $5 \times 10^8$ bacteria per ml), exponentially growing cells were coinfected with a 10-fold excess of lambda phage particles from the programmed library and a 5-fold excess of VCS-M13 helper phage. After a 30-min incubation, infected bacteria were diluted into 1 liter of fresh prewarmed medium supplemented with tetracycline. To select for bacteria infected with both viral particles, the antibiotics kanamycin (25 μg/ml) and ampicillin (100 ug/ml) were added to the cultures 30 min later. Cultures were then incubated an additional 8 to 16 h before phage particles were harvested.

To isolate phage DNA, bacterial cells were pelleted and phage-containing supernatants were precipitated with one-fourth volume of 3.5M ammonium acetate, pH 7.5, containing 20% polyethylene glycol at 4° C. To ensure that all the expected DNA molecules were synthesized, DNA extracted from an aliquot of the precipitated material was analyzed on agarose gels before the phagemid and lambda phage particles were separated by CsCl gradient centrifugation.

The precipitated phage were collected by centrifugation for 15 min at 10,000 × g and resuspended in 20 ml of SM buffer (50 mM Tris-HCl, pH 7.5, 20 mM MgSO4, 100 mM NaCl, 0.1% gelatin). Solid CsCl was added to 0.5 g/ml, and phage particles were banded by centrifugation at 4° C. for 18 to 24 h in a Beckman SW41 rotor at 30,000 rpm. Phagemids collected as a viscous band near the top of the gradient, whereas lambda particles were found in a lower more diffuse band. Phagemids were dialyzed against buffer (50 mM Tris-HCl, pH 8.0, 10 mM NaCl; 10 mM MgCl2) for 2 to 3 h at room temperature. The dialyzed material was then treated for 15 min at 37° C. with 2 μg of pancreatic DNase and RNase per ml, followed by the addition of EDTA (20 mM, pH 8.0). 0.5% sodium dodecyl sulfate (SDS), and 50 μg of proteinase K per ml. After 30 min at 65° C., extractions with phenolchloroform and chloroform were performed and the DNA was collected by ethanol precipitation. From 1 liter of culture up to 1 mg of closed circular single-stranded DNA (ssDNA) was obtained. The ssDNA consists of VCS-M13+helper phage DNA, ssDNA containing cloned cDNA sequences, and a small amount of SK(−) ssDNA lacking inserts. $^3$H-labeled ssDNA was prepared from bacterial cells grown in the presence of [methyl-$^3$H]thymidine (1 μCi/ml; specific activity=6.7 Ci/mmol). $^{125}$I-labeled ssDNA was prepared by using the protocol of Chikaraishi et al. (Cell 13:111–120 (1978)).

Closed circular ssDNA lacking cDNA inserts [SK(−)ssDNA] was obtained by infecting XL1-Blue cells transformed with the pBluescript plasmid SK(−) (Stratagene Cloning Systems) with VCS-M13 helper phage. After an overnight incubation, phagemid DNA was purified by using the Stratagene protocol for isolation of ssDNA. Helper phage DNA was separated from SK(−) ssDNA by chromatography on Sephacryl S-1000 (see FIG. 3, lane c). VCS-M13 ssDNA was prepared from host XL1-Blue cells infected with helper phage alone and was purified as just described. The large-scale preparation of lambda DNA from the amplified control library phage stock was done by using standard procedures (Maniatis, et al., Cold Spring Harbor Laboratory, Cold Spring Harbor, N.Y. (1982)).

EXAMPLE 5

In Vitro RNA Transcription

Purified lambda DNA synthesized from the control library was linearized with EcoRI when T3 polymerase was used and XbaI when T7 polymerase was used. Digestions were repeated twice to ensure complete linearization of template. After the second digestion, reactions were incubated 15 min at 37° C. with proteinase K (50 μg/ml), followed by extraction with phenolchloroform and chloroform alone. Digested template DNA was collected by ethanol precipitation and in resuspended diethyl pyrocarbonate (DEPC)-treated water at 0.5 to 1 μg/ml.

Transcription reactions (200 μl) were routinely done with 15 to 20 μg of template DNA in commercially provided transcription buffer containing 1.125 mM NTPs, RNase inhibitor (1 U/μl), and 1 mM dithiothreitol. T3 polymerase (Stratagene Cloning Systems) or T7 polymerase (Bethesda Research Laboratories) was added (50 U per reaction), and mixtures were incubated 90 min at 37° C. An additional 100 U of RNase inhibitor and 50 U of polymerase were added, and incubations were continued an additional 60 min. Samples were then treated with 20 U of RNAse-free DNase for 30 min, and the synthesized RNA was purified by phenolchloroform extraction and ethanol precipitation. Precipitated RNA was quantitated by $A_{260}$ and stored at −70° C. in DEPC-treated water. From a typical reaction containing 20 ug of template DNA, up to 100 μg of copy RNA was obtained. RNA (50 to 100 μg) was labeled with photobiotin (Sigma Chemical Co.) according to the protocol of Welcher et al. (Nucleic Acids Res. 14:10027–10043 (1986)) except that the amount of photobiotin used in the reaction was reduced to half the mass of the RNA.

EXAMPLE 6

Subtractive Hybridization

To construct the subtracted library, biotinylated copy RNA (150 μg) and ssDNA preparation (30 μg), of which one-fourth was estimated to be ssDNA containing cDNA inserts were coprecipitated in ethanol with 0.3M sodium acetate, pH 5.2. Precipitates were collected in siliconized microcentrifuge tubes (14,000 × g for 15 min), washed with 70% ethanol in TE buffer, and repelleted. Final pellets were dried and dissolved in 2× PIPES hybridization buffer {0.1M PIPES [piperazine-N,N'-bis(2-ethanesulfonic acid)], pH 6.8, 1.2M NaCl, 2 mM EDTA, 0.2% SDS}, and an equal volume of deionized formamide was added to the hybridization mixture. Samples were heated at 95° C. for 1 min and then incubated at 42° C. until the desired $C_0t$ value was achieved. Alternatively, material was first dissolved in $H_2O$ and then diluted with an equal volume of 2× hybridization solution. Hybridizations in these solutions were performed at 65° C. in sealed glass capillary tubes.

To separate unhybridized (subtracted ssDNA) from hybridized sequences, reactions were diluted 10 to 15 times with streptavidin binding buffer (10 mM Tris-HCl, pH 7.4, 400 mM NaCl, 2 mM EDTA) and incubated with streptavidin (Sigma Chemical Co.) for 30 min at 60° C. Streptavidin was added at a mass equal to the mass of copy RNA driving the hybridization. An equal volume of equilibrated phenolchloroform was added to the mixture, and phases were separated by centrifugation. The aqueous phase was carefully withdrawn and subjected to a second phenol-chloroform extraction followed by a final chloroform extraction. When the subtracted ssDNA was used for polymerase chain reaction (PCR) amplification and cloning, the subtracted material was either treated with RNase A for 15 min at 37° C. or incubated 60 min at 65° C. in 0.2 N NaOH to remove trace amounts of copy RNA. Material was again phenol-chloroform and chloroform extracted and recovered by ethanol precipitation with yeast tRNA added as a carrier. Final pellets were resuspended in 10 to 20 μl of 0.1 × TE buffer and stored at −20° C.

EXAMPLE 7

PCR Amplification Of Subtracted ssDNA

Approximately 2 to 5 ng of subtracted ssDNA from the programmed library was amplified by PCR (Saiki, et al., Science 230:1350–1354 (1985)). Reaction mixtures contained Taq polymerase buffer, 0.2 mM each dNTPs, 25 to 30 pmol of primers, and 2.5 U of Taq polymerase. Primers used for the specific amplification of cloned sequences were the oligo(dT)-XbaI primer used in first-strand cDNA synthesis and the universal M13 sequencing primer. Primer annealings were conducted at 31° C. for 5 cycles followed by 25 cycles at 48° C. Amplified PCR-generated DNA was purified by extraction first with phenol-chloroform and then with chloroform.

EXAMPLE 8

Construction And Screening Of Subtracted Libraries

The PCR-amplified sequences were digested with both XbaI and EcoRI and ligated into similarly digested pBluescript vector KSM13(+). Ligation reactions were diluted fourfold with sterile $H_2O$, and small amounts were used to transform high-efficiency XL1-Blue competent cells (Stratagene Cloning Systems) or DH5α competent cells (Bethesda Research Laboratories) by using the supplier's recommended protocol. To screen the subtracted library, transformation mixtures were plated directly onto nitrocellulose filters overlaid onto agar plates containing the appropriate antibiotics, 10 mM IPTG (isopropyl-β-D-thiogalactopyranoside) and 80 U of X-Gal (5-bromo-4-chloro-3-indolyl-β-D-galactopyranoside) per ml. Replicate filters were prepared by direct transfer of bacterial colonies onto a second prewetted nitrocellulose filter (Maniatis, et al., Cold Spring Harbor Laboratory, Cold Spring Harbor, N.Y. (1982)). A master plate and two filters were prepared in this manner from each transformation. Cells were prepared for hybridization by the protocol of Grunstein and Wallis (Methods Enzymol. 68:379–389 (1979)). In some screens, individual colonies of different transformations were consolidated onto a single plate from which replicate filters were prepared for use in hybridization with probe cDNA. Filters were first incubated for 4 to 6 h at 42° C. in hybridization solution containing 50% formamide, 4× SSPE (1 × SSPE is 0.18M NaCl, 10 mM NAPO4) and 1 mM EDTA, pH 7.7), buffer, 0.1% SDS, herring sperm DNA (200 μg/ml) and 50× Denhardt's solution, and then hybridization was conducted for 48 to 72 h (6 ml/150 mm filter) in solution containing $1 \times 10^6$ to $2 \times 10^6$ cpm of control cDNA (specific activity = $3 \times 10^8$ to $5 \times 10^8$ dpm/μg) per ml or $0.5 \times 10^6$ to $1 \times 10^6$ cpm of subtracted cDNA ($5 \times 10^8$ to $8 \times 10^8$ dpm/μg) per ml. RNA isolated from thymocytes incubated for 8 h with both dexamethasone and cycloheximide was used in preparing the subtracted cDNA probe. Following hybridization, filters were washed at increasing temperatures in 2× SSC-0.02% SDS and 0.2 × SSC-0.2% SDS (1 × SSC is 0.15M NaCl plus 0.015M sodium citrate). Final stringency washes were done for 30 min at 65° C.

EXAMPLE 9

Synthesis Of cDNA Probes

To synthesize cDNA for probing the subtracted library, 1 to 2 μg of polyadenylated RNA was collected by ethanol precipitation and resuspended in 5 μl of DEPC-treated water containing 0.4, ug of oligo(dT) primer. After being heated 5 min at 65° C., RNA and primer were transferred to a tube containing 200 to 400 μCi of [$^{32}$P]dCTP (>3,000 Ci/mmol). 40 μM cold dCTP, and 0.5 mM remaining dNTPs, 2 U of RNase inhibitor per μl, reverse transcriptase buffer, 50 μg of actinomycin D per ml. and 5 U of reverse transcriptase. The final reaction volume was 20 μl, and reactions were incubated 60 min at 37° C. Probes were purified by phenol-chloroform extractions and ethanol precipitation in the presence of 2.2M ammonium acetate. The cDNA was then incubated 1 to 2 h in 0.1 N NaOH at 65° C., neutralized, and reprecipitated in ethanol. Probes synthesized from control cell RNA were resuspended in a small volume of water and added directly to the hybridization solution. Subtracted probes were prepared by hybridizing cDNA generated from mRNA of cells incubated for 8 h in media containing dexamethasone and cycloheximide, the experimental cell mRNA, to a 10-fold excess of control thymocyte mRNA until a Cot value of 1,200 to 1,700 was attained. Unhybridized cDNA was recovered by hydroxylapatite chromatography alkali treated, and precipitated by the addition of ethanol.

EXAMPLE 10

Northern (RNA) Blot Analysis

Indicated amounts (see figure legends) of total cytoplasmic or polyadenylated cytoplasmic RNA were separated in 1.0 to 1.2% agarose gels and transferred to nylon membranes as described by Fourney et al. (Focus 10:5–7 (1988)).

EXAMPLE 11

DNA Sequence Determination cDNA clones were sequenced by the dideoxy-chain termination protocol using a modified form of T7 polymerase (Sequenase; U.S. Biochemical). Primary cDNA sequences were derived from clones isolated from the "death-induced" Lambda Zap libraries, not the PCR-generated subtracted libraries, and sequences presented here were obtained by sequencing both cDNA strands. This was achieved by sequencing overlapping subclones from the plasmid pKSM13(+) and by using cDNA-specified oligonucleotides as primers.

All sequence analyses and identification of structural motifs were done with the PC/Gene software program (Intelligenetics, Inc.). The most updated GenBank and EMBL nucleic acid data banks and the Swiss-Prot protein data bank were searched through the Internet network by using the FASTA program of Pearson and Lippman (Proc. Natl. Acad. Sci. U.S.A. 85:2444–2448 (1988)).

EXAMPLE 12

Expression Of RP-8 In Thymus

The expression of RP-8 genes in vivo before and after treatment with dexamethasone was examined to determine if RP-8 was present in all thymocytes or restricted to a subset of the population. Therefore, in situ hybridization was used to follow both the temporal and spatial distribution of these mRNAs.

Rats or mice were injected intraperitoneally with 5 mg dexamethasone per kg body weight and were kept up to 270 minutes before being sacrificed by $CO_2$. Thymuses were rapidly dissected and fixed by immersion in buffered 4% paraformaldehyde. Tissue was frozen and sectioned for hybridization with sense and antisense oligonucleotides. The antisense oligos represent RP-8 sequences that are 95–100% homologous between rat and mouse. When thymic sections from a control and experimental mouse were hybridized to a RP-8 antisense oligonucleotide, a hybridization pattern was shown. Clusters of RP-8 positive cells were observed in cortical regions of the thymus, particularly at the border of cortex and medulla. Occasionally, labeled cells were also found well within the medulla. There was a dramatic increase in the number of RP-8 labeled cells at 120 minutes after dexamethasone injection. In a more quantitative study, similar but less dramatic increases in RP-8 mRNA were observed in rat thymuses from about 90–270 minutes after steroid injection.

In both the mouse and rat, RP-8 was detected in isolated single cells and also in groups of adjacent cells. By looking at sections less exposed than those shown, there appeared to be 3–4 cells per group. Single labeled cells and cell clusters were scattered amongst mostly unlabeled cells. Several controls were used to establish the specificity of hybridization to the RP-8 antisense oligonucleotide. The hybridization signal in the thymus was competed out with cold antisense RP-8 oligonucleotide and a sense oligonucleotide of similar Tm did not display this pattern of hybridization. Additionally, a similar hybridization pattern was observed using an antisense oligo representing a different portion of the RP-8 sequence.

The intense pattern of hybridization seen in the thymus was not observed in a normal adult liver, a tissue that under normal conditions turns over at a very slow rate. Typically, 0–2 labeled cells per section were seen (about 5,000 cells) which is similar to the number of apoptoic cells (0–2 per 2,000–3,000 cells) reported for normal liver (Bursch et al., Carcinogenesis 11:847–853 (1990)). Based on their location, most of the labeled cells appeared to be hepatocytes although the possibility cannot be eliminated that at least some of the labeled cells in the liver might be infiltrating lymphocytes. With the control sense probe, no labeled cells were detected in three different sections (15,000 cells).

RP-8 expression in different adult tissues also has been observed by Northern blot analysis. RP-8 was detected in every tissue examined (brain, liver, kidney, lung, muscle, heart, and spleen) at levels below that found in thymocytes.

The pattern of RP-8 expression in thymus is consistent with the appearance of apoptosis. The mRNA is not present in most cortical thymoctes, but rather is found in isolated cells or in small groups of cells. In vivo administration of steroids results in an increase in RP-8 cells that is similar to the twofold induction of RP-8 mRNA observed in vitro. Most RP-8 expressing cells in untreated thymocytes were found at the interface between cortex and medulla. The majority of immature thymocytes within the thymus populate the cortex whereas mature T cells are found in the medulla. The junction between cortex and medulla may represent a zone of normal cell death with the thymus. When observed, RP-8 levels appear very high within individual cells expressing the mRNA. In tissues such as liver and adult brain where cell death normally occurs infrequently, only a few cells expressing RP-8 mRNA were detected.

EXAMPLE 13

RP-8 Expression in Weaver Mice Correlated With Death Of Granule Cell Precursor Cells An example of cell death in the CNS is the death of precursors to granule cell neurons that occur in mice homozygous for the weaver mutation. Progenitors to granule cell neurons proliferate normally in the external germinal layer (EGL) of weaver mice but fail to differentiate and migrate to their normal position in the internal granule cell layer. Consequently, the majority of these cells die by apoptosis in the inner region of the EGL (Smyne & Goldwitz, J. Neurosci. 9:1608–1620 (1989)) or just below it in the molecular layer. Death begins during the first postnatal week and continues until about P20.

When cerebellums from 8–10 day old weaver mice were probed with the RP-8 antisense probe, heavily labeled cells were scattered throughout the inner regions of the EGL. Consistent with the cessation of cell proliferation and death in weaver cerebellum, RP-8 positive cells were not as numerous by P17 and absent by P24. Labeled neurons were also found in the globus pallidus, striatum, and substantia nigra of 10 day old weaver mice.

These results clearly correlate RP-8 expression with cell death in the CNS. The appearance of RP-8 positive cells is precisely where degenerating granule cell progenitors are seen in weaver cerebellum. The identity of RP-8 positive cells as granule cells is confirmed by double labeling experiments using an antibody to the cell surface glycoprotein L1. Of further significance is the expression of RP-8 in isolated neurons of the substantia nigra and striatum, a second region of known cell death in weaver mice (Graybiel and Roffler-Tarlov, J. Neurosci. 10:720–733 (1990)). Histological stains confirm the presence of apoptotic cells in the globus pallidus since extensive cell death has not been reported in this region.

EXAMPLE 14

RP-8 Expression In the Rat Olfactory Epithelium

There is a continuous turnover of cells in the adult olfactory epithelium (Graziadei & Monte-Graziadei, J. Neurocytology 8:1–18 (1979)), particularly in the basal region where newly generated immature olfactory receptors are located (Farbman, et al., J. Neuroscience. 8:3281 (1988)). To determine whether RP-8 was expressed in a subset of olfactory cells, tissue sections also were probed through the rat olfactory epithelium.

Labeled cells were observed in cells near the basal layer of the olfactory epithelium. Labeled cells were not seen in this region with a control sense probe.

EXAMPLE 15

RP-8 Expression In Hematopoietic Cell Lines

The cell lines surveyed for RP-8 expression included S49.1 cells and CTLL-2s. S49.1 cells are a murine lymphoma cell line that are killed by glucocorticoids (Wyllie et al, Int. Rev. Cytol. 17:755–785 (1984)) and CTLL-2s are a killer T cell line dependent on IL-2 for proliferation and survival (Duke and Cohen, J. Immunol. 132:38–42 (1986)).

Small increases in RP-8 mRNA were observed 10–16 hours after induction in both cell lines. RP-8 mRNA was observed in untreated cells from both lines. In situ hybridizations determine that RP-8 expression in untreated cells is restricted to a small fraction of the total cell population. This result is consistent with the low level of death ongoing in these cell lines.

EXAMPLE 16

Synthesis Of RP-8 and RP-2 Fusion Proteins Using Bacterial Expression Vectors Several bacterial expression vectors were available in which the RP-8 and RP-2 cDNAs were expressed. The vectors that were used to generate RP-8 fusion proteins for antibody preparation are summarized below.

pET Expression Vectors

In these plasmid expression vectors cDNA sequences are cloned behind a T7 phage promoter and initiation codon and are thus transcribed by T7 RNA polymerase, a highly efficient and specific RNA polymerase (Rosenberg et al, Gene. 56:125 (1987)). Large quantities of fusion protein are obtained using this expression system. The specific vector for expression, peT5t, has multiple cloning sites. Fusion proteins synthesized from this vector contain 12–28 amino acids of vector sequence and are highly insoluble. Milligram quantities of several fusion proteins have been purified from inclusion bodies (Nagai and Thogerson, Methods in Enzym. 153:461 (1987)) derived from this expression system.

pBluescript Vectors

These vectors, commercially available from Stratgene Inc. are also expression vectors in which transcription of cDNAs are under control of the lac promoter. Fusion proteins are induced by incubation for 3–4 hours with IPTG. This vector has been used to obtain RP-8 fusion protein from inclusion body preparations.

RP-8 fusion protein has already been purified in mg quantities from standard inclusion body preparations and solubilized in detergent buffer (Harlow & Lane, Antibodies, A Laboratory Manual, Cold Spring Harbor Laboratory, N.Y. (1988)). If additional purification is required from that described above, elution from polyacrylamide gels or conventional chromatography is employed. Methods for immunization and antibody purification are well established (Harlow & Lane, Antibodies, A Laboratory Manual, Cold Spring Harbor Laboratory, N.Y. (1988)). Immunizations are done at a minimum of 4 week intervals using 100–200 ug purified fusion protein suspended in RIBI adjuvant (RIBI Research inc., Hamilton, MT). Injections and bleedings are taken 10–14 days after immunizations. To obtain the cleanest possible reagents for EM and light microscopy studies, affinity purified antibodies are obtained from antisera raised in rabbits using purified fusion protein as the absorbent by coupling of the antigen to an activated support such as Sepharose CL-4B. Purified fusion proteins are used to generate monoclonal antibodies to obtain highly specific RP-8 antibodies.

To obtain antibodies to RP-2 and RP-8, the cDNAs were cloned in the correct translational reading frame into bacterial expression vectors. RP-8 was cloned into the pBluescript SKM13(−) vector from Stratagene, Inc. and RP-2 was cloned into both pBluescript SKM13(−) and a derivative of the pPET expression vectors described by Studier. The RP-8 construct encoded an IPTG inducible fusion protein of 40 kd and RP-2 encoded a 26 kd fusion protein. Taking into account that 25 amino acids of the hybrid protein represent B-galactosidase, sequences the size of the RP-8 fusion protein are close to that predicted from the calculated molecular weight (32,000) of the RP-8 cDNA open reading frame. Similarly the electrophoretic migration of the RP-2 fusion protein is what would be expected, based on the calculated molecular weight of 23 kd for RP-2. Milligram quantities of fusion protein were then purified from inclusion body preparations and injected intramuscularly into rabbits using RIBI adjuvant. The immune sera for each protein is used to characterize and purify the relevant proteins from the thymus.

As will be apparent to those skilled in the art in which the invention is addressed, the present invention may be embodied in forms other than those specifically disclosed above without departing from the spirit or essential characteristics of the invention. The particular embodiments of the present invention described above, are, therefore, to be considered in all respects as illustrative and not restrictive. The scope of the present invention is as set forth in the appended claims rather than being limited to the examples contained in the foregoing description.

---

What is claimed is:

1. A polypeptide in substantially pure form and mutants and variants of the polypeptide eliciting programmed mammalian cell death, wherein the amino acid sequence is coded for by the DNA sequence set out in FIG. 5 (SEQ ID NO:1).

2. A polypeptide in substantially pure form and mutants and variants of the polypeptide eliciting programmed mammalian cell death, wherein the amino acid sequence is coded for by the DNA sequence set out in FIG. 6 (SEQ ID NO:3).

* * * * *

SEQUENCE LISTING ( 1 ) GENERAL INFORMATION:

(iii) NUMBER OF SEQUENCES: 4

(2) INFORMATION FOR SEQ ID NO:1:

(i) SEQUENCE CHARACTERISTICS:
    (A) LENGTH: 972 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..864

(xi) SEQUENCE DESCRIPTION: SEQ ID NO:1:

| | | | | | | | | | | | | | | | | |
|---|---|---|---|---|---|---|---|---|---|---|---|---|---|---|---|---|
| CCG | CTC | GCC | TTC | CTG | CTG | CAA | GTG | TAC | GCA | CCG | CTT | CCG | GGT | CGG | GAC | 48 |
| Pro | Leu | Ala | Phe | Leu | Leu | Gln | Val | Tyr | Ala | Pro | Leu | Pro | Gly | Arg | Asp | |
| 1 | | | | 5 | | | | | 10 | | | | | 15 | | |
| GAC | GCC | TTC | CAC | CGT | AGC | CTC | TTT | CTC | TTC | TGC | TGT | CGA | GAG | CCG | CTG | 96 |
| Asp | Ala | Phe | His | Arg | Ser | Leu | Phe | Leu | Phe | Cys | Cys | Arg | Glu | Pro | Leu | |
| | | | 20 | | | | | 25 | | | | | 30 | | | |
| TGT | TGC | GCC | GGC | CTG | CGA | GTT | TTT | CGT | AAT | CAG | CTA | CCA | AGG | AAA | AAT | 144 |
| Cys | Cys | Ala | Gly | Leu | Arg | Val | Phe | Arg | Asn | Gln | Leu | Pro | Arg | Lys | Asn | |
| | | 35 | | | | | 40 | | | | | 45 | | | | |
| GCA | TTT | TAC | TCA | TAT | GAG | CCC | CCT | TCT | GAA | ACG | GGA | GCT | TCG | GAT | ACA | 192 |
| Ala | Phe | Tyr | Ser | Tyr | Glu | Pro | Pro | Ser | Glu | Thr | Gly | Ala | Ser | Asp | Thr | |
| | 50 | | | | | 55 | | | | | 60 | | | | | |
| GAA | TGT | GTG | TGC | CTC | CAA | CTT | AAG | TCT | GGA | GCT | CAT | CTC | TGC | AGG | GTT | 240 |
| Glu | Cys | Val | Cys | Leu | Gln | Leu | Lys | Ser | Gly | Ala | His | Leu | Cys | Arg | Val | |
| 65 | | | | | 70 | | | | | 75 | | | | | 80 | |
| TGT | GGT | TGC | TTG | GCC | CCT | ATG | ACA | TGC | TCT | AGG | TGC | AAA | CAG | GCA | CAT | 288 |
| Cys | Gly | Cys | Leu | Ala | Pro | Met | Thr | Cys | Ser | Arg | Cys | Lys | Gln | Ala | His | |
| | | | | 85 | | | | | 90 | | | | | 95 | | |
| TAC | TGC | AGC | AAG | GAA | CAT | CAG | ACA | TTA | GAC | TGG | CAG | CTC | GGC | CAC | AAG | 336 |
| Tyr | Cys | Ser | Lys | Glu | His | Gln | Thr | Leu | Asp | Trp | Gln | Leu | Gly | His | Lys | |
| | | | 100 | | | | | 105 | | | | | 110 | | | |
| CAG | GCT | TGT | ACA | CAG | TCA | GAC | CAT | TTA | GAC | CAT | ATG | GTT | CCA | GAC | CAT | 384 |
| Gln | Ala | Cys | Thr | Gln | Ser | Asp | His | Leu | Asp | His | Met | Val | Pro | Asp | His | |
| | | 115 | | | | | 120 | | | | | 125 | | | | |
| AAC | TTG | CTG | TTT | CCA | GAA | TTT | GAA | ATT | GTA | ACA | GAA | ACA | GAA | GAC | GAG | 432 |
| Asn | Leu | Leu | Phe | Pro | Glu | Phe | Glu | Ile | Val | Thr | Glu | Thr | Glu | Asp | Glu | |
| | 130 | | | | | 135 | | | | | 140 | | | | | |
| ATT | GGG | CCT | GAG | GTG | GTG | GAA | ATG | GAG | GAT | TAC | TCT | GAA | GTT | ATA | GGA | 480 |
| Ile | Gly | Pro | Glu | Val | Val | Glu | Met | Glu | Asp | Tyr | Ser | Glu | Val | Ile | Gly | |
| 145 | | | | | 150 | | | | | 155 | | | | | 160 | |
| AGC | ATG | GAG | GGA | GTA | CCT | GAG | GAA | GAA | CTA | GAT | TCC | ATG | GCA | AAG | CAT | 528 |
| Ser | Met | Glu | Gly | Val | Pro | Glu | Glu | Glu | Leu | Asp | Ser | Met | Ala | Lys | His | |
| | | | | 165 | | | | | 170 | | | | | 175 | | |
| GAA | TCC | AAG | GAA | GAT | CAC | ATA | TTC | CAA | AAG | TTT | AAA | TCC | AAA | ATA | GCC | 576 |
| Glu | Ser | Lys | Glu | Asp | His | Ile | Phe | Gln | Lys | Phe | Lys | Ser | Lys | Ile | Ala | |
| | | | 180 | | | | | 185 | | | | | 190 | | | |
| CTT | GAA | CCA | GAG | CAG | ATT | CTC | AGG | TAT | GGA | AGA | GGT | ATT | AAA | CCC | ATC | 624 |
| Leu | Glu | Pro | Glu | Gln | Ile | Leu | Arg | Tyr | Gly | Arg | Gly | Ile | Lys | Pro | Ile | |
| | | 195 | | | | | 200 | | | | | 205 | | | | |
| TGG | ATT | TCT | GGT | GAA | AAT | ATT | CCT | CAA | GAA | AAA | GAT | ATT | CCA | GAT | TGC | 672 |
| Trp | Ile | Ser | Gly | Glu | Asn | Ile | Pro | Gln | Glu | Lys | Asp | Ile | Pro | Asp | Cys | |
| | 210 | | | | | 215 | | | | | 220 | | | | | |
| TCA | TGT | GGT | GTT | AAG | AGA | ATA | TTT | GAA | TTC | CAG | GTC | ATG | CCT | CAG | CTG | 720 |
| Ser | Cys | Gly | Val | Lys | Arg | Ile | Phe | Glu | Phe | Gln | Val | Met | Pro | Gln | Leu | |
| 225 | | | | | 230 | | | | | 235 | | | | | 240 | |
| TTG | AAC | CAC | CTT | AAG | GCA | GAC | AGA | CTG | GGT | ACA | AGT | GTG | GAC | TGG | GGC | 768 |
| Leu | Asn | His | Leu | Lys | Ala | Asp | Arg | Leu | Gly | Thr | Ser | Val | Asp | Trp | Gly | |

```
                              245                          250                            255
ATC TTG GCT GTC TTC ACC TGT GCT GAG AGC TGC AGC CTG GGC ATC GGG      816
Ile Leu Ala Val Phe Thr Cys Ala Glu Ser Cys Ser Leu Gly Ile Gly
            260                     265                 270

TTC ACA GAA GAA TTT GTG TGG AAA CAG GAT GTG ACA GAG ACA CCA TGAAAGGTG 871
Phe Thr Glu Glu Phe Val Trp Lys Gln Asp Val Thr Glu Thr Pro
        275                     280                 285

TAAATTCTTA AAAATAAATG TTCCTTATGC CTCACTACCT CAAAAAAAAA AAAAAAAAA     931

AAAAAAAAAA AAAAAAAAAA AAAAAAAAAA AAAAAAAAAA A                        972
```

( 2 ) INFORMATION FOR SEQ ID NO:2:

( i ) SEQUENCE CHARACTERISTICS:
        ( A ) LENGTH: 287 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Pro Leu Ala Phe Leu Leu Gln Val Tyr Ala Pro Leu Pro Gly Arg Asp
 1               5                  10                  15

Asp Ala Phe His Arg Ser Leu Phe Leu Phe Cys Cys Arg Glu Pro Leu
            20                  25                  30

Cys Cys Ala Gly Leu Arg Val Phe Arg Asn Gln Leu Pro Arg Lys Asn
            35                  40                  45

Ala Phe Tyr Ser Tyr Glu Pro Pro Ser Glu Thr Gly Ala Ser Asp Thr
        50                  55                  60

Glu Cys Val Cys Leu Gln Leu Lys Ser Gly Ala His Leu Cys Arg Val
65                  70                  75                  80

Cys Gly Cys Leu Ala Pro Met Thr Cys Ser Arg Cys Lys Gln Ala His
                85                  90                  95

Tyr Cys Ser Lys Glu His Gln Thr Leu Asp Trp Gln Leu Gly His Lys
                100                 105                 110

Gln Ala Cys Thr Gln Ser Asp His Leu Asp His Met Val Pro Asp His
            115                 120                 125

Asn Leu Leu Phe Pro Glu Phe Glu Ile Val Thr Glu Thr Glu Asp Glu
        130                 135                 140

Ile Gly Pro Glu Val Val Glu Met Glu Asp Tyr Ser Glu Val Ile Gly
145                 150                 155                 160

Ser Met Glu Gly Val Pro Glu Glu Glu Leu Asp Ser Met Ala Lys His
                165                 170                 175

Glu Ser Lys Glu Asp His Ile Phe Gln Lys Phe Lys Ser Lys Ile Ala
            180                 185                 190

Leu Glu Pro Glu Gln Ile Leu Arg Tyr Gly Arg Gly Ile Lys Pro Ile
        195                 200                 205

Trp Ile Ser Gly Glu Asn Ile Pro Gln Glu Lys Asp Ile Pro Asp Cys
    210                 215                 220

Ser Cys Gly Val Lys Arg Ile Phe Glu Phe Gln Val Met Pro Gln Leu
225                 230                 235                 240

Leu Asn His Leu Lys Ala Asp Arg Leu Gly Thr Ser Val Asp Trp Gly
                245                 250                 255

Ile Leu Ala Val Phe Thr Cys Ala Glu Ser Cys Ser Leu Gly Ile Gly
            260                 265                 270

Phe Thr Glu Glu Phe Val Trp Lys Gln Asp Val Thr Glu Thr Pro
        275                 280                 285
```

( 2 ) INFORMATION FOR SEQ ID NO:3:

( i ) SEQUENCE CHARACTERISTICS:
　　( A ) LENGTH: 878 base pairs
　　( B ) TYPE: nucleic acid
　　( C ) STRANDEDNESS: single
　　( D ) TOPOLOGY: linear ( i i ) MOLECULE TYPE: DNA (genomic)

( i x ) FEATURE:
　　( A ) NAME/KEY: CDS
　　( B ) LOCATION: 1..636

( x i ) SEQUENCE DESCRIPTION: SEQ ID NO:3:

| CCC | CAG | CTG | GCA | CAT | GGC | TGC | TAC | CCA | TGC | CCT | CCA | CAC | AGG | CGC | AAC | 48 |
| Pro | Gln | Leu | Ala | His | Gly | Cys | Tyr | Pro | Cys | Pro | Pro | His | Arg | Arg | Asn | |
| 1 | | | | 5 | | | | | 10 | | | | | 15 | | |

| CTG | GTA | GAG | GAG | GTG | AAC | GGC | ACC | TAC | ATG | AAG | AAG | TGC | CTC | TAT | CAC | 96 |
| Leu | Val | Glu | Glu | Val | Asn | Gly | Thr | Tyr | Met | Lys | Lys | Cys | Leu | Tyr | His | |
| | | | 20 | | | | | 25 | | | | | 30 | | | |

| AAG | ATT | CAA | CAC | CCC | CTG | TGC | CCA | GTC | TTC | AAC | CTT | GGC | TAT | GTG | GTG | 144 |
| Lys | Ile | Gln | His | Pro | Leu | Cys | Pro | Val | Phe | Asn | Leu | Gly | Tyr | Val | Val | |
| | | 35 | | | | | 40 | | | | | 45 | | | | |

| CGA | GAG | TCA | GGC | CAG | GAC | TTC | CGC | AGC | CTT | GCT | GAG | AAG | GGT | GGG | GTG | 192 |
| Arg | Glu | Ser | Gly | Gln | Asp | Phe | Arg | Ser | Leu | Ala | Glu | Lys | Gly | Gly | Val | |
| | 50 | | | | | 55 | | | | | 60 | | | | | |

| GTT | GGT | ATC | ACC | ATT | GAC | TGG | AAG | TGT | GAT | CTG | GAC | TGG | CAC | GTT | CGG | 240 |
| Val | Gly | Ile | Thr | Ile | Asp | Trp | Lys | Cys | Asp | Leu | Asp | Trp | His | Val | Arg | |
| 65 | | | | | 70 | | | | | 75 | | | | | 80 | |

| CAC | TGC | AAA | CCC | ATC | TAC | CAG | TTC | CAC | GGA | CTG | TAT | GGG | GAG | AAG | AAC | 288 |
| His | Cys | Lys | Pro | Ile | Tyr | Gln | Phe | His | Gly | Leu | Tyr | Gly | Glu | Lys | Asn | |
| | | | | 85 | | | | | 90 | | | | | 95 | | |

| CTG | TCT | CCA | GGC | TTC | AAC | TTC | AGA | TTT | GCC | AGG | CAT | TTC | GTG | CAG | AAT | 336 |
| Leu | Ser | Pro | Gly | Phe | Asn | Phe | Arg | Phe | Ala | Arg | His | Phe | Val | Gln | Asn | |
| | | | 100 | | | | | 105 | | | | | 110 | | | |

| GGG | ACA | AAC | CGT | CGC | CAC | CTC | TTC | AAG | GTG | TTT | GGG | ATT | CAC | TTT | GAT | 384 |
| Gly | Thr | Asn | Arg | Arg | His | Leu | Phe | Lys | Val | Phe | Gly | Ile | His | Phe | Asp | |
| | | 115 | | | | | 120 | | | | | 125 | | | | |

| ATC | CTT | GTG | GAT | GGC | AAG | GCT | GGG | AAG | TTT | GAC | ATC | ATC | CCT | ACT | ATG | 432 |
| Ile | Leu | Val | Asp | Gly | Lys | Ala | Gly | Lys | Phe | Asp | Ile | Ile | Pro | Thr | Met | |
| | 130 | | | | | 135 | | | | | 140 | | | | | |

| ACT | ACT | ATC | GGT | TCT | GGG | ATT | GGC | ATC | TTT | GGA | GTG | GCC | ACA | GTG | CTT | 480 |
| Thr | Thr | Ile | Gly | Ser | Gly | Ile | Gly | Ile | Phe | Gly | Val | Ala | Thr | Val | Leu | |
| 145 | | | | | 150 | | | | | 155 | | | | | 160 | |

| TGT | GAT | CTC | TTA | TTG | CTC | CAC | ATC | CTG | CCT | AAG | AGG | CAC | TAC | TAC | AAG | 528 |
| Cys | Asp | Leu | Leu | Leu | Leu | His | Ile | Leu | Pro | Lys | Arg | His | Tyr | Tyr | Lys | |
| | | | | 165 | | | | | 170 | | | | | 175 | | |

| CAG | AAG | AAG | TTC | AAA | TAT | GCC | GAG | GAC | ATG | GGG | CCG | GGA | GAG | GGT | GAA | 576 |
| Gln | Lys | Lys | Phe | Lys | Tyr | Ala | Glu | Asp | Met | Gly | Pro | Gly | Glu | Gly | Glu | |
| | | | 180 | | | | | 185 | | | | | 190 | | | |

| CAT | GAC | CCC | GTG | GCC | ACC | AGC | TCC | ACT | CTG | GGC | CTG | CAG | GAG | AAC | ATG | 624 |
| His | Asp | Pro | Val | Ala | Thr | Ser | Ser | Thr | Leu | Gly | Leu | Gln | Glu | Asn | Met | |
| | | 195 | | | | | 200 | | | | | 205 | | | | |

| AGG | ACC | TCC | TGACCTTAGT | CTTGAGATCC | GGACTTGACG | CAGTGTGTGG | | | 673 |
| Arg | Thr | Ser | | | | | | | |
| | | 210 | | | | | | | |

| CTTCCGGCAA | GGGCTGATGG | CTTTGAGCCA | GGGCAGAGGG | CATTCCAGA | GGCTTTCCCT | 733 |
| GCAAGGCAGA | CACCAGTGGC | CCTCTGGTTC | AGCATGAAGA | CAGGCAAGAC | TTTGGATTTC | 793 |
| ATAGCTCTGG | TTTCAGTTCC | ACATGTCCCT | TCCTGAGGGA | TGCCTCCTCC | AGTTTCTCC | 853 |
| AATTTGGGTT | CATATGGCTG | GGCCC | | | | 878 |

( 2 ) INFORMATION FOR SEQ ID NO:4:

(i) SEQUENCE CHARACTERISTICS:
   (A) LENGTH: 211 amino acids
   (B) TYPE: amino acid
   (D) TOPOLOGY: linear (ii) MOLECULE TYPE: protein (xi) SEQUENCE DESCRIPTION: SEQ ID NO:4:

```
Pro Gln Leu Ala His Gly Cys Tyr Pro Cys Pro Pro His Arg Arg Asn
 1               5                  10                  15

Leu Val Glu Glu Val Asn Gly Thr Tyr Met Lys Lys Cys Leu Tyr His
             20                  25                  30

Lys Ile Gln His Pro Leu Cys Pro Val Phe Asn Leu Gly Tyr Val Val
         35                  40                  45

Arg Glu Ser Gly Gln Asp Phe Arg Ser Leu Ala Glu Lys Gly Gly Val
     50                  55                  60

Val Gly Ile Thr Ile Asp Trp Lys Cys Asp Leu Asp Trp His Val Arg
 65                  70                  75                  80

His Cys Lys Pro Ile Tyr Gln Phe His Gly Leu Tyr Gly Glu Lys Asn
                 85                  90                  95

Leu Ser Pro Gly Phe Asn Phe Arg Phe Ala Arg His Phe Val Gln Asn
             100                 105                 110

Gly Thr Asn Arg Arg His Leu Phe Lys Val Phe Gly Ile His Phe Asp
         115                 120                 125

Ile Leu Val Asp Gly Lys Ala Gly Lys Phe Asp Ile Ile Pro Thr Met
     130                 135                 140

Thr Thr Ile Gly Ser Gly Ile Gly Ile Phe Gly Val Ala Thr Val Leu
145                 150                 155                 160

Cys Asp Leu Leu Leu Leu His Ile Leu Pro Lys Arg His Tyr Tyr Lys
             165                 170                 175

Gln Lys Lys Phe Lys Tyr Ala Glu Asp Met Gly Pro Gly Glu Gly Glu
             180                 185                 190

His Asp Pro Val Ala Thr Ser Ser Thr Leu Gly Leu Gln Glu Asn Met
         195                 200                 205

Arg Thr Ser
     210
```